United States Patent [19]

Baldwin et al.

[11] Patent Number: 4,735,956

[45] Date of Patent: Apr. 5, 1988

[54] CERTAIN 1,4-DIHYDRO-2,6-DI-LOWER HYDROCARBYL-4-HETEROCYCLIC-3,5-PYRIDINE DICARBOXYLATES WHICH ARE USEFUL AS CALCIUM CHANNEL BLOCKERS

[75] Inventors: John J. Baldwin, Gwynedd Valley; Wasyl Halczenko, Hatfield; George D. Hartman, Lansdale; Brian T. Phillips, Telford, all of Pa.

[73] Assignee: Merck & Co., Inc., Rahway, N.J.

[21] Appl. No.: 775,869

[22] Filed: Sep. 13, 1985

[51] Int. Cl.[4] .................. C07D 401/04; C07D 413/04; C07D 417/04; A61K 31/44

[52] U.S. Cl. ..................................... 514/338; 546/270; 546/271; 546/277

[58] Field of Search ...................... 546/270, 271, 277; 514/338

[56] References Cited

U.S. PATENT DOCUMENTS

| | | | |
|---|---|---|---|
| 3,905,970 | 9/1975 | Bossert et al. | 544/82 |
| 3,923,818 | 12/1975 | Bossert et al. | 546/321 |
| 4,044,147 | 8/1977 | Bossert et al. | 514/150 |
| 4,237,137 | 12/1980 | Tacke et al. | 514/256 |
| 4,285,955 | 8/1981 | Wehinger et al. | 514/356 |
| 4,622,332 | 11/1986 | Wehinger et al. | 514/356 |

*Primary Examiner*—Alan L. Rotman
*Attorney, Agent, or Firm*—Salvatore C. Mitri; Michael C. Sudol; Mario A. Monaco

[57] ABSTRACT

Novel substituted 4-heteroaryl-1,4-dihydropyridine compounds useful as calcium channel blockers, pharmaceutical compositions thereof, and methods of treatment are disclosed.

7 Claims, No Drawings

CERTAIN 1,4-DIHYDRO-2,6-DI-LOWER HYDROCARBYL-4-HETEROCYCLIC-3,5-PYRIDINE DICARBOXYLATES WHICH ARE USEFUL AS CALCIUM CHANNEL BLOCKERS

BACKGROUND OF THE INVENTION

Substituted dihydropyridines are known to be useful for reducing blood pressure, effecting dilation of the coronary vessels, and preventing urospasms. Typical of such substituted dihydropyridines are those disclosed in U.S. Pat. Nos. 3,923,818; 3,905,970; 4,044,141; 4,237,137; and 4,285,955.

DESCRIPTION OF THE INVENTION

The present invention is directed to a compound of the formula:

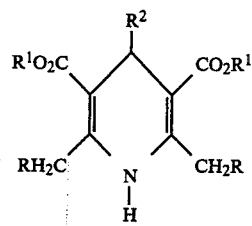

wherein, $R^1$, is a straight or branched chain, saturated or unsaturated hydrocarbon having 1 to 8 carbon atoms;

R, is hydrogen or $R^1$; and $R^2$, is a heteroaryl selected from the group consisting of:

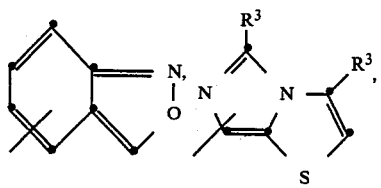

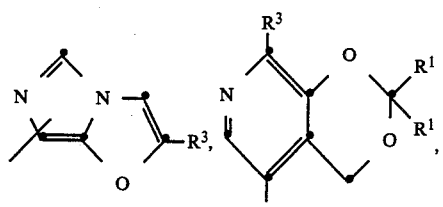

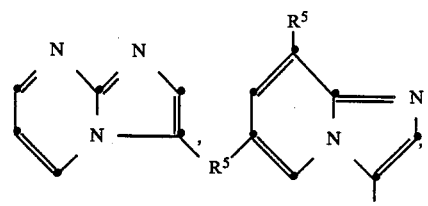

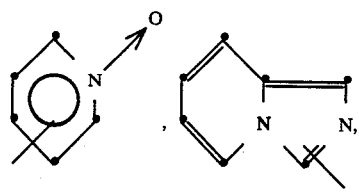

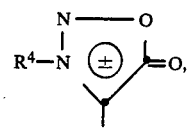

wherein, $R^1$ is as defined above;

$R^3$, is selected from hydrogen, alkyl $C_1$-$C_6$, phenyl, or phenyl alkyl $C_1$-$C_6$;

$R^4$ is selected from alkyl $C_1$-$C_6$, phenyl or phenyl alkyl $C_1$-$C_6$;

$R^5$ is $R^3$, chlorine or bromine; and pharmaceutically acceptable salts thereof.

The point of attachment, in the above bicyclic rings with a floating bond, may be in either ring.

The preferred compounds are:

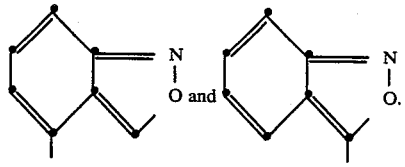

The most preferred is

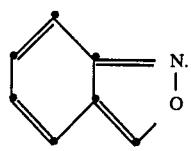

The present invention is also directed to those novel intermediates which are used to produce the above compounds. These compounds include aldehydes of the following formulas:

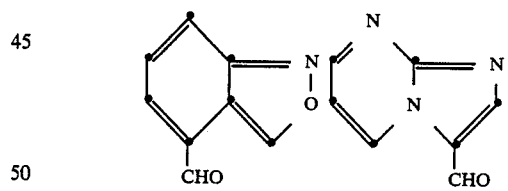

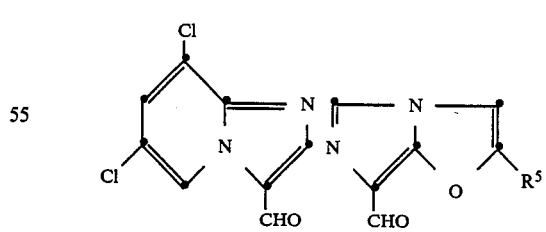

wherein $R^5$ is hydrogen, alkyl $C_{1-6}$, phenyl, phenyl alkyl $C_{1-6}$, chlorine, or bromine.

The pharmaceutically acceptable salts are those acid addition salts of non-toxic, pharmaceutically acceptable acids and include salts of inorganic acids such as hydrochloric, hydrobromic, hydroiodic, phosphoric, sulfuric, nitric and the like, and organic acids such as trifluoroacetic and trichloroacetic and the like and include acids relating to the pharmaceutically acceptable salts listed in Journal of Pharmaceutical Science, 66, 2 (1977) and incorporated herein by reference.

As indicated above, the compounds of this invention are useful as calcium channel blockers, and thus have broad pharmacological utility in that they exhibit (i) pronounced and long-lasting vasodilating effect accompanied by an energy-sparing effect on cardiac metabolism; (ii) antiarrhythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory system; (vi) useful antihypercholesterolemic and antilipidemic action; (vii) protection of the ischemic myocardium; (viii) inhibition of irritable bowel syndrome and esophageal spasm; or, (ix) inhibition of migraine. Some of these compounds are also useful cardiotonic agents.

The representative compounds of the present invention were found to inhibit vascular calcium contraction, reduce cardiac contractile force, inhibit calcium-mediated tracheal contraction, inhibit calcium uptake in pituitary cells, or displace membrane bound tritiated nitrendepine.

The compounds of the present invention can be administered in any suitable form; e.g. orally, sublingually, transdermally, or parenterally; i.e. intravenously, interperitoneally, etc. Thus, the compounds can be offered in a form (a) for oral administration e.q. as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., nitroglycerine tablets, lactose tablets, and the like, for rapid dissolution or high molecular weight methylcellulose tablets, carboxymethylcellulose tablets, and the like, for slower, time-releasing delivery; or, (c) for parenteral administration e.g. dissolved or dispersed in a suitable liquid carrier or emulsified.

The pharmaceutical preparations thus described are made following the conventional techniques of the pharmaceutical chemist as appropriate to the desired end product.

The ratio of active compound to compounding ingredients i.e. carrier, diluent etc. will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or β-blocking agents. For example, the compounds of this invention can be given in combination with such compounds as enalapril, hydralazine hydrochloride, hydrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The compounds of the invention are prepared by reacting the aromatic aldehyde with an alkyl 3-aminoacrylate, such as methyl 3-aminocrotonate, and an alkyl acylacetate, such as methyl acetoacetate, in a solvent (preferably alcohols and hydrocarbons) at elevated temperatures (preferably reflux) until the reaction is completed (usually 1 to 24 hours). Alternatively, these compounds could be prepared by reacting the aromatic aldehyde with an alkyl acylacetate and ammonium hydroxide as described in Example 14.

The following Examples are provided to further illustrate the best mode currently known for preparing the compounds and compositions of this invention, but are not to be construed as limiting this invention in any manner.

EXAMPLE 1

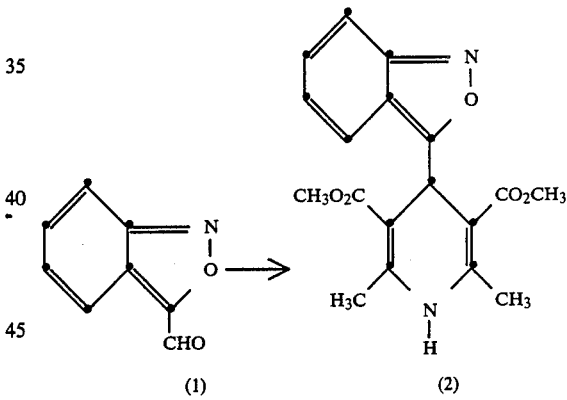

Dimethyl 4-[3-(2,1-benzisoxazolyl)]-2,6-dimethyl-1,4-dihydropyridine-3,5-dicarboxylate (2)

A solution of 0.29 g (2.0 mmoles) 3-formyl-2,1-benzisoxazole (1), 0.23 g (2.0 mmoles) methyl acetoacetate and 0.23 g (2.0 mmoles) methyl 3-aminocrotonate in 2 ml isopropanol was refluxed for 4 hours. The mixture was cooled and the resulting precipitate was filtered off to give 0.47 g (69%) crude product which was recrystallized from ethanol to give 0.35 g (51%) (2), m.p. 237°–238°; ir (potassium bromide pellet): 3450, 3330, 1680, 1640, 1490, 1430, 1220, 1120, 1020, 800, 750 cm$^{-1}$; nmr (deuteriochloroform): 2.3 (s, 6H), 3.6 (s, 6H), 5.7 (s, 1H), 7.4 (m, 4H), 9.4 (br s, 1H).

Anal. Calcd. for $C_{18}H_{18}N_2O_5$: C, 63.15; H, 5.30; N, 8.18. Found: C, 63.12; H, 5.42; N, 8.22.

EXAMPLE 2

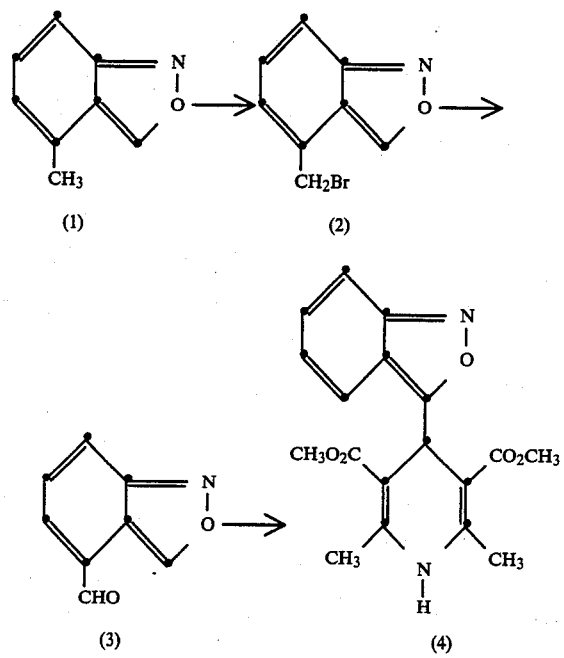

4-Methyl-2,1-benzisoxazole (1)

To a solution of 49.64 g (220 mmoles) stannous chloride dihydrate in 132 ml concentrated hydrochloric acid cooled to 15° was added 9.08 g (55.0 mmoles) of 6-methyl-2-nitrobenzaldehyde with rapid stirring. After 2 hours the mixture was diluted with 250 ml water and extracted with 3×150 ml ether. The extract was washed successively with dilute sodium bicarbonate solution, water, and brine, dried, and concentrated to give 6.78 g oil. The oil was flash chromatographed, eluting with chloroform to give 6.10 g (83%) (1) as an oil; nmr (deuteriochloroform): 2.5 (s, 3H), 6.7 (dd, 1H), 7.3 (m, 2H), 9.1 (s, 1H).

4-Bromomethyl-2,1-benzisoxazole (2)

To a solution of 5.99 g (45.0 mmoles) (1) in 135 ml carbon tetrachloride was added 8.81 g (49.5 mmoles) N-bromosuccinimide and 100 mg benzoyl peroxide. The mixture was refluxed while illuminated by a 250 watt sunlamp for 18 hours. The mixture was cooled and filtered, and the filtrate concentrated to give 9.9 g of a dark red oil. The oil was extracted with 500 ml hot hexane. The hexane solution was evaporated to 150 ml and cooled to give 6.60 g (69%) of crystalline (2), m.p. 51.0°-52.5°; nmr (deuteriochloroform): 4.6 (s, 2H), 7.2 (m, 3H), 9.3 (s, 1H).

Anal. Calcd for $C_8H_6BrNO$: C, 45.31; H, 2.85; N, 6.61. Found: C, 44.97; H, 2.62; N, 6.58.

4-Formyl-2,1-benzisoxazole (3)

Step 1. To a solution of 3.99 g (18.8 mmoles) (2) in 30 ml ether under nitrogen was added 1.49 g (18.8 mmoles) pyridine. A white precipitate formed and the mixture was stirred overnight. The precipitate was then filtered off, washed with ether, and dried to give 3.64 g (66%) 4-(2,1-benzisoxazolyl)methylpyridinium bromide, m.p. 172°-174°; nmr (DMSO-$d_6$): 6.3 (s, 2H), 7.5 (m, 3H), 8.2 (m, 2H), 8.9 (m, 1H), 9.6 (dd, 2H), 10.3 (s, 1H).

Step 2. At room temperature 12.5 ml (12.5 mmoles) of 1N sodium hydroxide was added to a suspension of 3.64 g (12.5 mmoles) of the pyridinium bromide and 1.88 g (12.5 mmoles) N,N-dimethyl-4-nitrosoaniline in 19 ml 95% ethanol, and the mixture was stirred overnight. Then 21 ml of 6N hydrochloric acid was added and, after stirring for 30 minutes, the resulting red solution was extracted with 3×150 ml ether. The ether extract was washed successively with dilute sodium bicarbonate solution, water, and brine, dried, and concentrated to give 1.50 g orange solid. The solid was flash chromatographed eluting with chloroform to give 1.32 g solid. Recrystallization from n-butyl chloride gave 0.94 g (51%) (3), m.p. 137°-141°; ir (chloroform): 2800, 1680 (C=O), 1630, 1400, 1080, 820 cm$^{-1}$; nmr (deuteriochloroform): 7.6 (m, 3H), 9.7 (s, 1H), 9.9 (s, 1H).

High resolution mass spectrum. Theoretical mass: 147.0320. Measured mass: 147.0321.

Dimethyl 4-[4-(2,1-benzisoxazolyl)]-2,6-dimethyl-1,4-dihydropyridine-3,5-dicarboxylate (4)

This compound (m.p. 211°-213°) was prepared in 21% yield from treatment of (3) with methyl acetoacetate and methyl 3-aminocrotonate; ir (potassium bromide pellet): 3350, 3150, 2950, 1660, 1480, 1430, 1330, 1300, 1210, 1110, 1040, 860 cm$^{-1}$; nmr (deuteriochloroform): 2.3 (s, 6H), 3.6 (s, 6H), 5.3 (s, 1H), 6.3 (br s, 1H), 6.9 (d, 1H, J=6 Hz), 7.3 (m, 2H), 9.3 (s, 1H).

Anal. Calcd. for $C_{18}H_{18}NO_5$: C, 63.15; H, 5.30; N, 8.18. Found: C, 62.96; H, 5.50; N, 8.05.

EXAMPLE 3

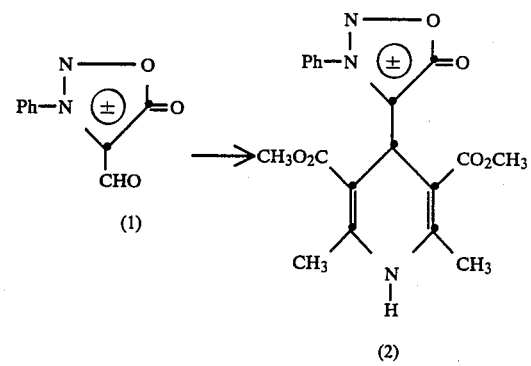

Dimethyl 2,6-dimethyl-4[4-(3-phenylsydnonyl)]-1,4-dihydropyridine-3,5-dicarboxylate (2)

To 0.19 g (1.0 mmol) 4-formyl-3-phenylsydnone (1) in 1 ml isopropanol was added 0.115 g (1 mmol) methyl 3-aminocrotonate and 0.115 g (1.0 mmol) methyl acetoacetate and the resulting solution heated at reflux for 4 hours. The cooled reaction mixture was filtered to give a tan solid which was washed with hot ethanol and then hot methanol to provide pure (2), m.p. 276°-277°.

EXAMPLE 4

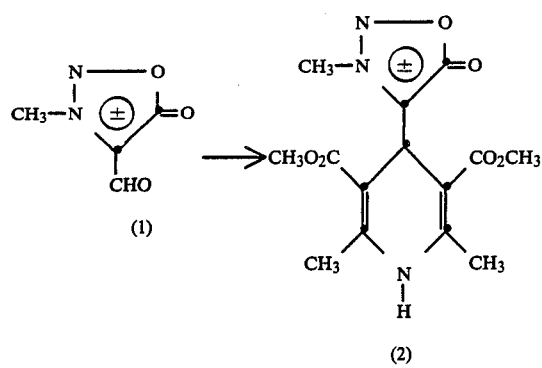

Dimethyl 2,6-dimethyl-4-[4-(3-methylsydnonyl)]-1,4-dihydropyridine-2,6-dicarboxylate (2)

To 0.13 g (1 mmol) 4-formyl-3-methylsydnone sydnone (1) in 1 ml isopropanol was added 0.115 g (1.0 mmol) methyl 3-aminocrotonate and 0.115 g (1.0 mmol) methyl acetoacetate and the resulting solution refluxed for 4 hours. The cooled reaction mixture was filtered and this solid was recrystallized from EtOH to provide pure (2), m.p. 276.5°–277.5°.

EXAMPLE 5

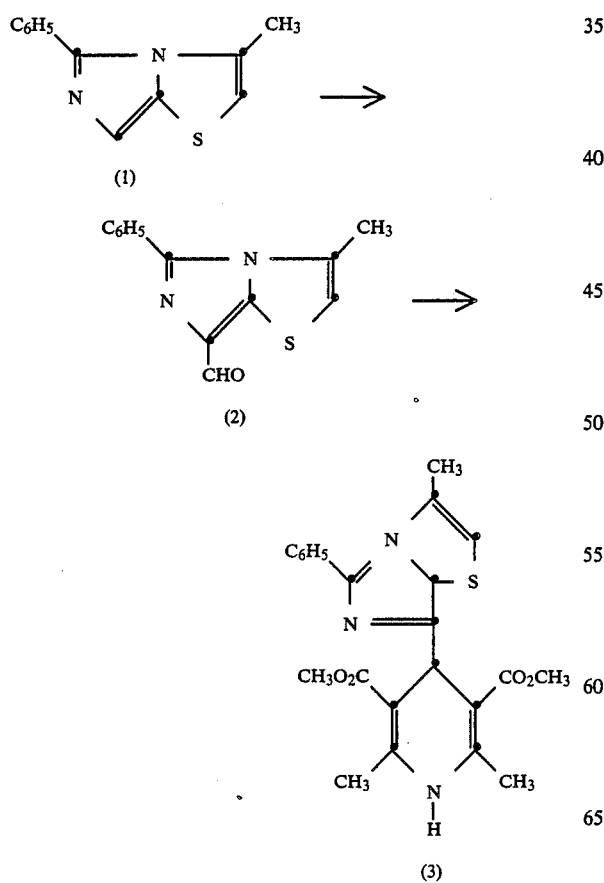

7-Formyl-3-methyl-5-phenylimidazo[5,1-b]thiazole (2)

To 40 ml DMF at 0° was added 7.0 ml POCl₃ dropwise over 15 minutes and the resulting solution allowed to stand for 15 minutes at room temperature. At 0° 6.0 g (0.028 mol) 3-methyl-5-phenyl-imidazo[5,1-b]thiazole (1) in 10 ml DMF was added dropwise and the resulting solution was stirred at room temperature overnight.

The reaction mixture was cooled, diluted with 150 ml CH₂Cl₂, made basic (pH 9) with saturated Na₂CO₃ solution and this was washed with 3×50 ml water. The organic extract was dried and the solvent removed in vacuo to afford (2).

Dimethyl 2,6-dimethyl-4-{7-(3-methyl-5-phenylimidazo-[5,1-b]thiazoyl)}-1,4-dihydropyridine-3,5-dicarboxylate (3)

To 0.25 g (1.0 mmol) (2) in 10 ml methanol was added 1.0 ml NH₄OH solution, 0.12 g (1 mmol) methyl 3-aminocrotonate and 0.12 g (1 mmol) methyl acetoacetate and the resulting solution was refluxed for 72 hours. The cooled reaction mixture was filtered to provide a white solid that was washed with 5 ml CH₃OH and then 5 ml ether to give pure (3), m.p. 259°–60°.

EXAMPLE 6

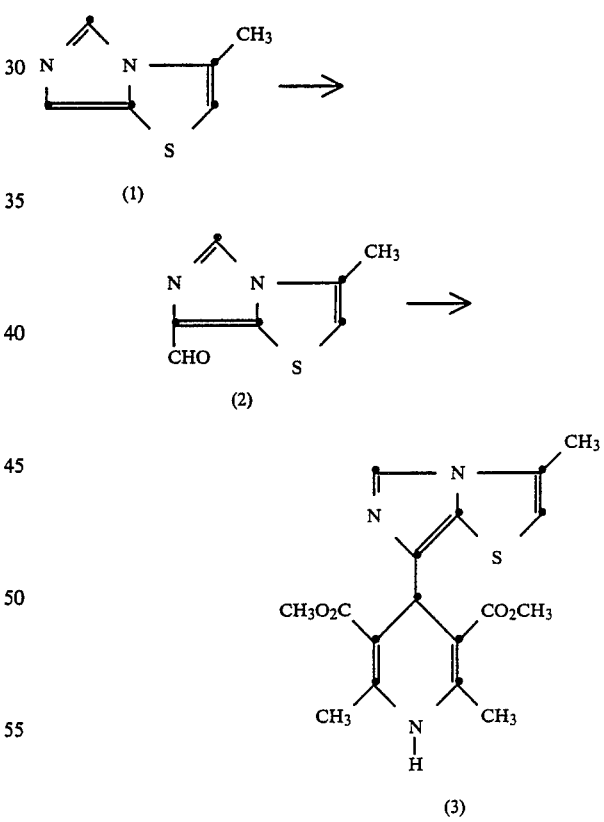

7-Formyl-3-methylimidazo[5,1-b]thiazole (2)

2.0 g (14.5 mmol) 3-methylimidazo[5,1-b]thiazole (1) was added dropwise to a solution of 6.13 g (40 mmol) phosphorus oxychloride in 35 ml DMF at 0° and the resulting solution was stirred at 0° for 0.5 hours, and then at room temperature overnight.

The reaction mixture was diluted with 125 ml water, made basic with 40% NaOH solution, and then extracted with 4×100 ml portions of CH₂Cl₂. The combined organic extracts were dried and the solvent removed in vacuo to give a yellow solid, collected by filtration, washed with ether to give (2), m.p. 172°–175°.

Dimethyl 2,6-dimethyl 4-7-{(3-methylimidazo[5,1-b]thiazolyl)}-1,4-dihydropyridine-3,5-dicarboxylate (3)

To 0.83 g (5 mmol) (2) in 10 ml methanol was added 0.5 ml NH₄OH solution, 0.58 g (5 mmol) methyl 3-aminocrotonate, and 0.58 g (5 mmol) methyl acetoacetate and the resulting solution refluxed for 18 hours. The cooled reaction mixture was filtered to give a white solid which was washed with 5 ml methanol to provide pure (3), m.p. 270°–272° (dec.).

EXAMPLE 7

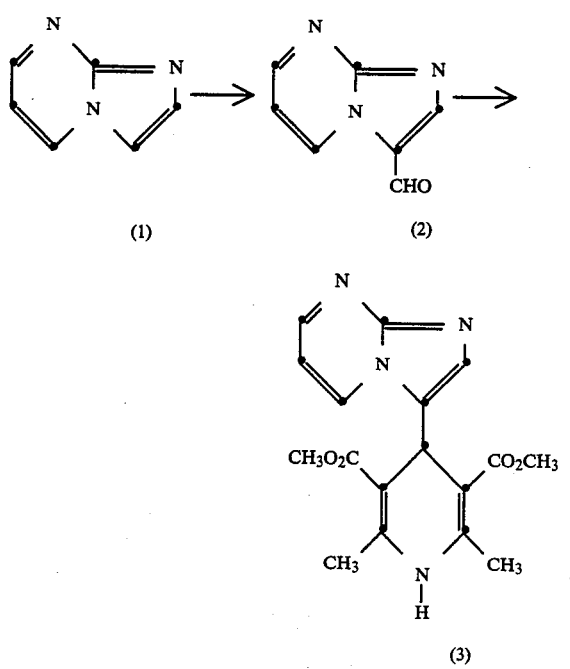

3-Formylimidazo[1,2-a]pyrimidine (2)

To 14 ml DMF cooled to 0° was added 6.0 g (0.039 mol) phosphorus oxychloride dropwise over 15 minutes, followed by 1.79 g (0.015 mol) imidazo[1,5-a]pyrimidine (1). The resulting mixture was heated at 120° for 0.5 hours and then at 90° for 5 hours. The cooled reaction mixture was then poured onto a mixture of ice water, made basic with 40% NaOH solution and then extracted with 4×100 ml portions of CH₂Cl₂. The combined organic extracts were dried and the solvent removed in vacuo to give crude (2). This was purified by chromatography on silica gel eluting with CH₂Cl₂ (97)-isopropanol (3) to give pure (2), m.p. 198°–200°.

Dimethyl 2,6-dimethyl-4-(3-imidazo[1,2-a]pyrimidinyl)-1,4-dihydropyridine-3,5-dicarboxylate (3)

To 0.5 g (3.4 mmol) (2) in 10 ml isopropanol was added 0.39 g (3.4 mmol) methyl 3-aminocrotonate and 0.39 g (3.4 mmol) methyl acetoacetate and the resulting solution refluxed overnight. The cooled reaction mixture was then diluted with 15 ml ether and stirred for 1 hour. The tan solid was filtered off and recrystallized from ethyl acetate to give pure (3), m.p. 202°–205° (dec).

EXAMPLE 8

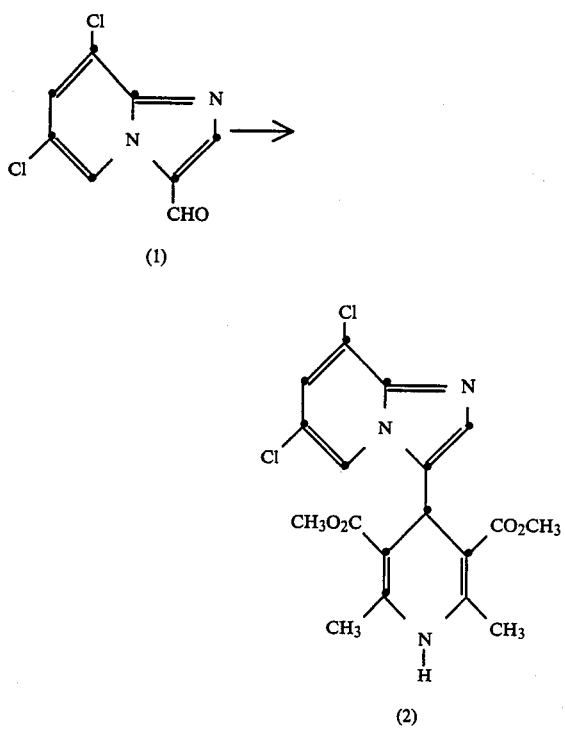

Dimethyl 2,6-dimethyl-4-{3[(6,8-dichloroimidazo[1,2-a]-pyridinyl)]}-1,4-dihydropyridine-3,5-dicarboxylate (2)

To 1.08 g (5 mmol) 6,8-dichloro-3-formylimidazo-[1,5-a]pyridine (1) in 15 ml isopropanol was added 0.58 g (5 mmol) methyl 3-aminocrotonate and 0.58 g (5 mmol) methyl acetoacetate and the resulting solution refluxed for 24 hours. The cooled reaction mixture was filtered to give a yellow solid that was triturated with 10 ml isopropanol and then recrystallized from CH₃OH-/isopropanol to give pure (2), m.p. 265°–268° (dec).

EXAMPLE 9

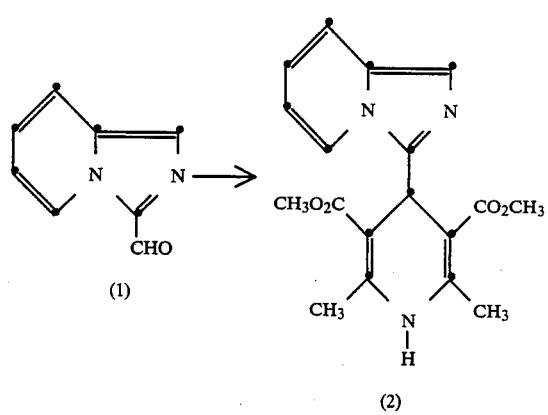

Dimethyl 2,6-dimethyl-4-(3-imidazo[1,5-a]pyridinyl)-1,4-dihydropyridine-3,5-dicarboxylate (2)

To 0.58 g (4 mmol) 3-formylimidazo[1,5-a]pyridine (1) in 15 ml isopropanol was added 0.46 g (4 mmol) methyl 3-aminocrotonate and 0.46 g (4 mmol) methyl acetoacetate and the resulting solution was heated at reflux for 20 hours. The cooled reaction mixture was then filtered to give a yellow solid which was washed with ether and subsequently recrystallized from methanol to give pure (2), m.p. 255°-257° (dec).

EXAMPLE 10

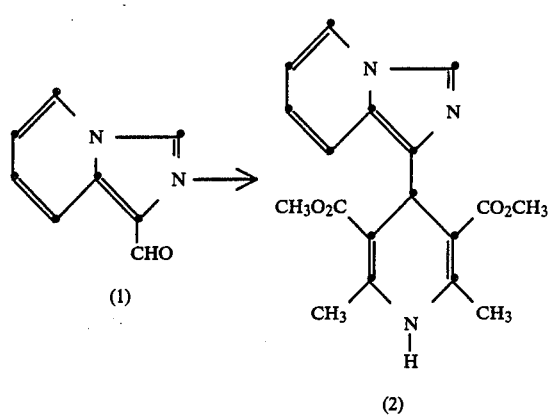

Dimethyl 2,6-dimethyl-4-(1-imidazo[1,5-a]pyridinyl)-1,4-dihydropyridine-3,5-dicarboxylate (2)

To 1.02 g (7 mmol) 1-formylimidazo[1,5-a]pyridine (1) in 20 ml isopropanol was added 0.81 g methyl 3-aminocrotonate and 0.81 g (7 mmol) methyl acetoacetate and the resulting solution refluxed for 14 hours. The cooled reaction mixture was filtered to give a yellow solid which was recrystallized from CH₃OH to afford pure (2), m.p. 265°-267° (dec).

EXAMPLE 11

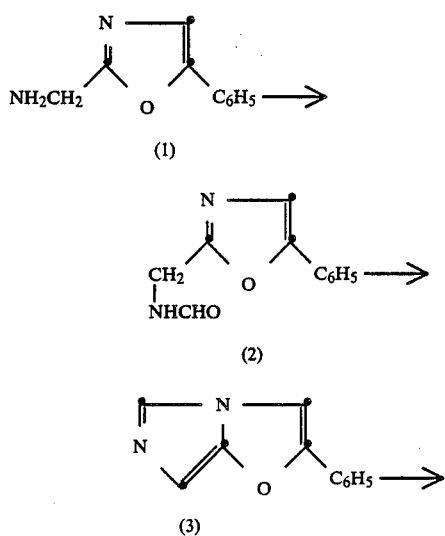

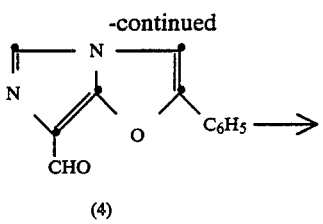

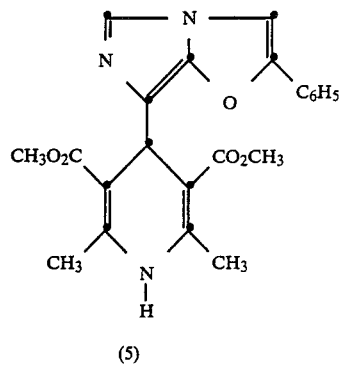

N-(5-phenyl-2-oxazolylmethyl)formamide (2)

To 0.5 g (2.9 mmol) 5-phenyl-2-oxazolylmethylamine (1) was added 10 ml ethyl formate and the resulting solution heated at reflux for 10 hours. The solvent was removed in vacuo to leave a viscous oil that crystallized upon standing. This crude (2) was used directly in the next reaction.

2-phenylimidazo[5,1-b]oxazole (3)

To 0.6 g (3 mmol) (2) in 15 ml toluene was added dropwise 1 ml phosphorus oxychloride and the resulting solution was heated at 90° overnight. Then, the solvent was removed in vacuo and the residue carefully diluted with 50 ml water. This solution was made basic with 40% NaOH solution and extracted with 4×50 ml portions of methylenechloride. The combined organic extracts were washed with brine, dried and the solvent removed in vacuo to give a dark gum. This was purified by chromatography on silica gel eluting with methylene chloride (97%)-isopropanol (3%) to give pure (3) as a waxy, tan solid, m.p. 128°-131° (dec).

4-Formyl-2-phenylimidazo[5,1-b]oxazole (4)

To 10 ml dimethylformamide cooled to 0° was added 1.84 g (12 mmol) phosphorus oxychloride dropwise with stirring over 15 minutes. Then, 0.77 g (4 mmol) 3 was added and the resulting solution was stirred at 0°-5°. After 10 minutes the ice bath was removed and the reaction mixture was stirred at room temperature overnight and then heated at 90° for 48 hours. The cooled reaction mixture was then poured into 75 ml cold water and this made basic with 40% sodium hydroxide solution. The dark solid that precipitated was collected, washed with water and sucked dry. This was taken up in 200 ml methylene chloride, washed with 50 ml brine, dried and the solvent removed in vacuo to give (4) as a brown solid, m.p. 190° (dec).

Dimethyl 2,6-dimethyl-4-{4-(2-phenylimidazo[5,1-b]oxazolyl)}-3,5-dicarboxylate (5)

To 0.43 g (2 mmol) 4 in 10 ml methanol was added 0.24 g (2.1 mmol) methyl 3-aminocrotonate and 0.24 g (2.1 mmol) methyl acetoacetate and the resulting solution was heated at reflux for 72 hours. The cooled reaction mixture was diluted with 20 ml ether and crude product was filtered off. This material was purified by chromatography on silica gel eluting with $CH_2Cl_2(95)$—$CH_3OH(5)$ to give pure (5), m.p. 215°–222° (dec).

EXAMPLE 12

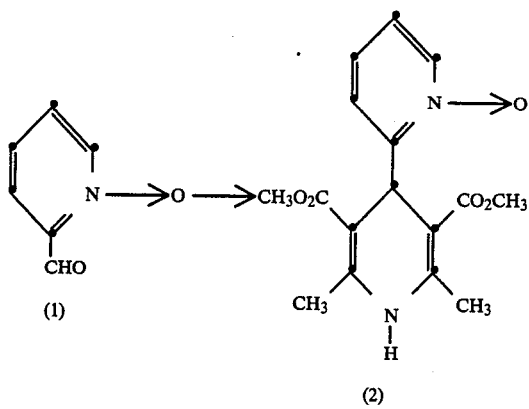

Dimethyl 2,6-dimethyl-4-(2-pyridinyl-N-oxide)-1,4-dihydropyridine-3,5-dicarboxylate To 0.78 g (5 mmol) 2-pyridine-N-oxide carboxaldehyde (1) in 15 ml methanol was added 0.58 g (5 mmol) methyl 3-aminocrotonate and 0.58 g (5 mmol) methyl acetoacetate and the resulting solution was refluxed for 18 hours. The cooled reaction mixture was filtered to give a yellow solid that was triturated with hexane to give pure (2), m.p. 225°–228°.

EXAMPLE 13

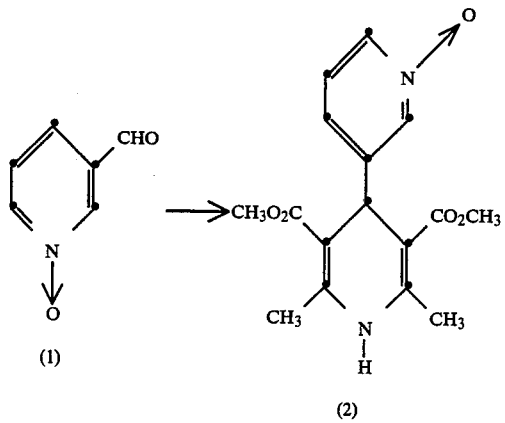

Dimethyl 2,6-dimethyl-4-(3-pyridinyl-N-oxide)-1,4-dihydropyridine-3,5-dicarboxylate (2)

To 0.74 g (6 mmol) 3-pyridine-N-oxide carboxaldehyde (1) in 15 ml methanol was added 0.69 g (6 mmol) methyl 3-aminocrotonate and 0.70 g (6 mmol) methyl acetoacetate and the resulting solution heated at reflux for 24 hours. The cooled reaction mixture was then filtered to remove the crude product. This was recrystallized from ethyl acetate to give 2, m.p. 225°–228°.

EXAMPLE 14

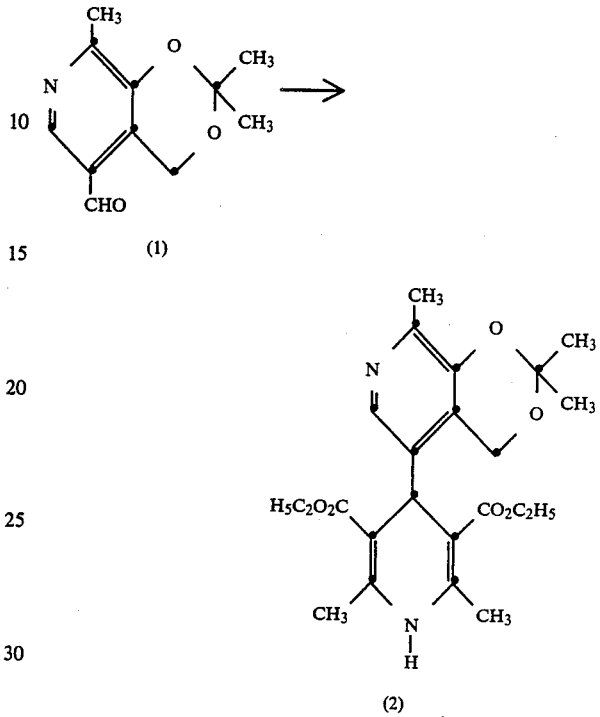

Diethyl 2,6-dimethyl-4-[5-(3,4-O-isopropylidene pyridoxyl)]-1,4-dihydropyridine-3,5-dicarboxylate (2)

To 0.95 g (4.6 mmol) 3,4-O-isopropylidene pyridoxal (1) in 15 ml ethanol was added 1.2 g (10.3 mmol) ethyl acetoacetate and 5 ml conc. $NH_4OH$ solution and the resulting mixture refluxed for 3 hours. The cooled reaction mixture was filtered and this solid was recrystallized from ethanol to afford pure (2), m.p. 240°–241°.

EXAMPLE 15

As a specific embodiment of a composition of this invention an active ingredient, such as dimethyl 4-[4-(2,1-benzisoxazolyl)]-2,6-dimethyl-1,4-dihydropyridine-3,5-dicarboxylate, is formulated to yield 5000 compressed tablets, each containing 50 mg of the active ingredient, as follows:
active ingredient: 250 grams
starch: 70 grams
dibasic calcium phosphate hydrous: 500 grams
calcium stearate: 2.5 grams

What is claimed is:

1. A compound of the formula:

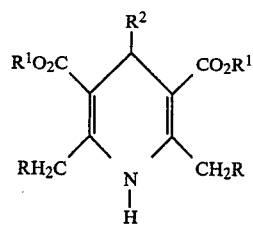

wherein, $R^1$, is a straight or branched chain, saturated or unsaturated hydrocarbon having up to 8 carbon atoms;

R, is hydrogen or $R^1$; and $R^2$ is a heteroaryl selected from the group consisting of:

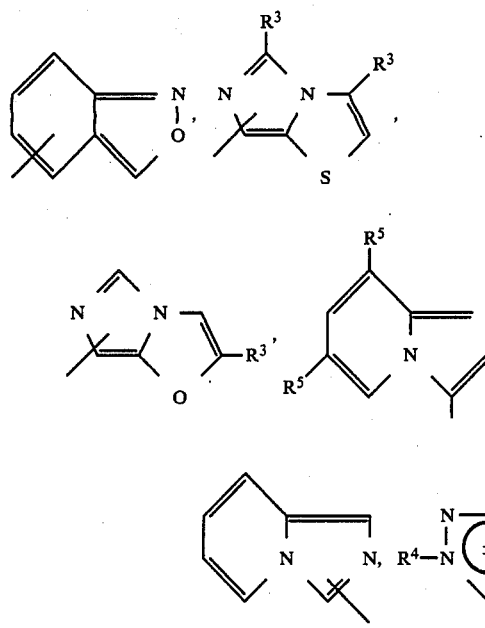

wherein, $R^1$ is as defined above;

$R^3$, which may be the same or different, is hydrogen, alkyl $C_{1-6}$, phenyl, or phenyl alkyl $C_{1-6}$;

$R^4$ is alkyl $C_{1-6}$, phenyl, or phenyl alkyl $C_{1-6}$;

$R^5$ is $R^3$, chlorine or bromine; or a pharmaceutically acceptable salt thereof.

2. The compound of claim 1, wherein $R^1$ is methyl or ethyl and R is hydrogen.

3. The compound of claim 2, wherein $R^2$ is selected from the group consisting of:

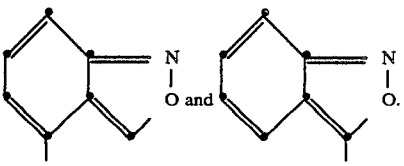

4. The compound of claim 3, which is dimethyl 4-[4-(2,1-benzisoxazolyl)]-2,6-dimethyl-1,4-dihydropyridine-3,5-dicarboxylate.

5. The compound of claim 3, which is dimethyl 4-[3-(2,1-benzisoxazolyl]-2,6-dimethyl-1,4-dihydropyridine-3,5-dicarboxylate.

6. A compound of claim 1, which is selected from the group consisting of:
(a) dimethyl 2,6-dimethyl-4[4-(3-phenylsydnonyl)]-1,4-dihydropyridine-3,5-dicarboxylate;
(b) dimethyl 2,6-dimethyl-4-[4-(3-methylsydnonyl)]-1,4-dihydropyridine-2,6-dicarboxylate;
(c) dimethyl 2,6-dimethyl-4-7-(3-methyl-5-phenylimidazo[5,1-b]thiazoyl)-1,4-dihydropyridine-3,5-dicarboxylate;
(d) dimethyl 2,6-dimethyl 4-7-(3-methylimidazo[5,1-b]thiazoyl)-1,4-dihydropyridine-3,5-dicarboxylate;
(e) dimethyl 2,6-dimethyl-4-[4-(2-phenylimidazo[5,1-b]oxazoyl]-3,5-dicarboxylate.

7. A pharmaceutical composition useful as a calcium channel blocker comprising a nontoxic therapeutically effective amount of a compound of claim 1 in admixture with a pharmaceutically acceptable carrier.

* * * * *